US011446372B2

(12) United States Patent
Debrie et al.

(10) Patent No.: US 11,446,372 B2
(45) Date of Patent: Sep. 20, 2022

(54) BORDETELLA STRAINS EXPRESSING SEROTYPE 3 FIMBRIAE

(71) Applicants: Institut Pasteur de Lille, Lille (FR); Institut National de la Santé et de la Recherche Médicale (INSERM), Paris (FR)

(72) Inventors: Anne-Sophie Debrie, La Madeleine (FR); Dominique Raze, Gruson (FR); Camille Locht, Brussels (BE)

(73) Assignees: Institut Pasteur de Lille, Lille (FR); INSTITUT NATIONAL DE LA SANTÉ ET DE LA RECHERCHE MÉDICALE (INSERM), Paris (FR)

( * ) Notice: Subject to any disclaimer, the term of this patent is extended or adjusted under 35 U.S.C. 154(b) by 1 day.

(21) Appl. No.: 16/848,793

(22) Filed: Apr. 14, 2020

(65) Prior Publication Data

US 2020/0297833 A1 Sep. 24, 2020

Related U.S. Application Data

(63) Continuation of application No. PCT/EP2018/078522, filed on Oct. 18, 2018.

(60) Provisional application No. 62/574,068, filed on Oct. 18, 2017.

(51) Int. Cl.
*A61K 39/02* (2006.01)
*A61P 31/04* (2006.01)
*A61K 39/00* (2006.01)

(52) U.S. Cl.
CPC ............ *A61K 39/099* (2013.01); *A61P 31/04* (2018.01); *A61K 2039/522* (2013.01)

(58) Field of Classification Search
None
See application file for complete search history.

(56) References Cited

U.S. PATENT DOCUMENTS

| 4,883,761 | A | * | 11/1989 | Keith | C07K 14/235 |
| | | | | | 435/252.33 |
| 6,660,261 | B1 | * | 12/2003 | Mielcarek | A61P 37/04 |
| | | | | | 424/93.4 |
| 6,713,072 | B1 | | 3/2004 | Pizza | |
| 6,841,358 | B1 | | 1/2005 | Locht | |
| 9,119,804 | B2 | * | 9/2015 | Locht | A61P 31/04 |
| 9,180,178 | B2 | * | 11/2015 | Locht | A61K 39/099 |
| 9,415,077 | B2 | * | 8/2016 | Alonso | A61P 37/08 |
| 9,528,086 | B2 | * | 12/2016 | Locht | C07K 14/235 |
| 9,655,959 | B2 | * | 5/2017 | Alonso | A61K 39/099 |
| 9,730,995 | B2 | * | 8/2017 | Locht | A61P 31/04 |
| 10,258,681 | B2 | * | 4/2019 | Locht | A61K 39/099 |
| 10,369,207 | B2 | * | 8/2019 | Alonso | A61K 39/099 |
| 10,610,580 | B2 | * | 4/2020 | Locht | A61P 31/04 |
| 10,653,765 | B2 | * | 5/2020 | Locht | A61P 31/04 |
| 10,682,377 | B2 | * | 6/2020 | Solans | A61K 35/00 |
| 10,751,072 | B2 | * | 8/2020 | Kendall | A61M 37/0015 |
| 10,799,573 | B2 | * | 10/2020 | Brickman | C07K 14/235 |
| 11,065,276 | B2 | * | 7/2021 | Solans | A61K 9/007 |
| 11,110,161 | B2 | * | 9/2021 | Locht | A61K 39/099 |
| 2005/0147607 | A1 | | 7/2005 | Reed | |
| 2009/0246222 | A1 | | 10/2009 | Locht | |
| 2010/0111996 | A1 | | 5/2010 | Leclerc | |
| 2012/0121647 | A1 | | 5/2012 | Alonso | |
| 2013/0183336 | A1 | | 7/2013 | Locht | |
| 2017/0283890 | A1 | | 10/2017 | Solans et al. | |
| 2019/0175719 | A1 | * | 6/2019 | Locht | A61K 39/099 |
| 2019/0290903 | A1 | * | 9/2019 | Zarafshani | A61K 9/0009 |
| 2020/0171169 | A1 | * | 6/2020 | Duvall | A61K 47/32 |
| 2020/0206331 | A1 | * | 7/2020 | Kumar | A61K 39/292 |
| 2020/0297833 | A1 | * | 9/2020 | Debrie | A61P 31/04 |
| 2021/0290667 | A1 | * | 9/2021 | Solans | A61K 9/007 |

FOREIGN PATENT DOCUMENTS

| EP | 1184459 | A2 | | 3/2002 | |
| EP | 2442826 | | | 4/2012 | |
| EP | 1994139 | | | 7/2016 | |
| FR | 2718750 | | | 10/1995 | |
| WO | 9816553 | | | 4/1998 | |
| WO | 03102170 | | | 12/2003 | |
| WO | 2007104451 | | | 9/2007 | |
| WO | 2008118592 | | | 10/2008 | |
| WO | 2008156753 | | | 12/2008 | |
| WO | 2010125014 | | | 11/2010 | |
| WO | 2010146414 | | | 12/2010 | |
| WO | 2013066272 | | | 5/2013 | |
| WO | 2014060514 | | | 4/2014 | |
| WO | 2017167834 | | | 10/2017 | |
| WO | WO-2019077028 | A1 | * | 4/2019 | ............ A61P 31/04 |
| WO | 2020049133 | | | 3/2020 | |

OTHER PUBLICATIONS

Gorringe et al, Expert Rev. Vaccine, 2014, 13/10:1205-1214. (Year: 2014).*
Carbonetti, Current Opinion in Pharmacology, 2007, 7:272-278. available online: Apr. 5, 2007 (Year: 2007).*
Carbonetti. Future Microbiol., Mar. 2010. 5:455-469 (Year: 2010).*
Carbonetti. FEMS Pathogens and Disease, 2015, 73/8, 8 pages. (Year: 2015).*
Debrie et al, vaccine, 2018, 36:1345-1352. available online Feb. 9, 2018 (Year: 2018).*
Kilgore et al, Clinical Microbiology Reviews. Jul. 2016, 29/3:449-486. published Mar. 30, 2016 (Year: 2016).*
Li et al Bioengineered Bugs, 2011, 2:6, 315-319 (Year: 2011).*

(Continued)

*Primary Examiner* — Nita M. Minnifield
(74) *Attorney, Agent, or Firm* — Stanley A. Kim

(57) ABSTRACT

A Fim3-producing BPZE1 derivative with sufficiently stable fim3 expression to provide improved protection in mice against Fim3-only producing clinical *B. pertussis* isolates was developed. The fim3 expression in BPZE1f3 did not alter the protective efficacy against Fim2+ strains, nor against strains that produce neither Fim2 nor Fim3.

9 Claims, 6 Drawing Sheets

Specification includes a Sequence Listing.

(56) References Cited

OTHER PUBLICATIONS

Melvin et al, Nat. Rev. Microbiol., Apr. 2014, 12/4:274-288 (Year: 2014).*
Poulain-Godefroy et al, FEMS Immunol. Med. Microbiol., 2008, 54:129-136 (Year: 2008).*
Romero et al, Future Microbiology, 2014, 9/12:1339-1360 (Year: 2014).*
Scanlon et al, Adv. Exp. Med. Biol., 2019, 1183:35-51 (Year: 2019).*
Storsaeter et al, Expert Opion on Emerging Drugs, 2006, 11/2:195-205. (Year: 2006).*
Yusibov, V. et al.: "Peptide-based candidate vaccine against respiratory syncytial virus," Vaccine, 2005, vol. 23:2261-2265.
Walker, K. E. et al.: "Characterizationof the demnonecrotic toxin in members of the genus Bordetella," Infect. Immun., 1994, vol. 62, No. 9:3817-3828.
Teman, UA. et al.: "A novel role for murine IL-4 in vivo: induction of MUC5AC gene expression and mucin hypersecretion," Am J Respir Cell Mol Biol., 1997, vol. 16(4):471-478.
Stith, Rebecca et al.:"The link between tracheal cytotoxin production and peptidoglycan recycling in Bordetella Pertussis," Abstracts of the General Meeting of the American Society for Microbiology, New Orleans; 1996; vol. 96:184 (XP008013937).
Li, Rui, et. al.: "Attenuated Bordetella pertussis BPZE1 as a live vehicle for heterologous vaccine antigens delivery thorugh the nasal route," Bioengineered Bugs, 2011, vol. 2(6):315-319.
Li, Rui, et al.: "Development of live attenuated Bordetella pertussis strains expressing the universal influenza vaccine candidate M2e," Vaccine, 2011, vol. 29:L5502-5511.
Romagnani, Sergio, "Immunologic influences on allergy and the TH1/TH2 balance," J Allergy Clin Immunol, 2004, pp. 395-400.
Nemery, B. et al.: "Interstitial lung disease induced by exogenous agents: factors governing susceptibility," Eur Respir J, 2001, vol. 18, Suppl. 32:30s-42s.
Neirynck, Sabine, et al.: "A universal influenza A vaccine based on the extracellular domain of the M2 protein," Nature Medicine, 1999, vol. 5:1157-1163.
Nagel, Gabriele et al.: "Association of pertussis and measles infections and immunizations with asthma and allergic sensitization in ISAAC Phase Two," Pediatric Allergy and Immunology, 2012, vol. 23:736-745.
Morokata, T. et al.: "C57BL/6 mice are more susceptible to antigen-induced pulmonary eosinophilia than BALB/c mice, irrespective of systemic T helper 1/T helper 2 responses," Immunology, 1999, vol. 98:345-351.
Mielcarek, Nathalie et al.: "Homologous and heterologous protection after single intranasal administration of live attenuated recombinant Bordetella pertussis," Nature Biotechnology, 1998, vol. 16:454-457.
Marsland, B.J., et al.: "Allergic airway inflammation is exacerbated during acute influenza infection and correlates with increased allergen presentation and recruitment of allergen-specific T-helper type 2 cells," Clinical & Experimental Allergy, 2004, vol. 34, Issue 8.
Mahon, B., et al.: "Atypical Disease after Bordetella pertussis Respiratory Infection of Mice with Targeted Disruptions of Interferon-γ Receptor or Immunoglobulin μ Chain Genes," J. Exp. Med., 1997, vol. 186, No. 11:1843-1851.
Locht, Camille, et al.: "Bordetella pertussis: from functional genomics to intranasal vaccination," Iny. J. Med. Microbiol., 2004, vol. 293:583-588.
Li, Z.M., et al.: "Cloning and sequencing of the structural gene for the porin protein of Bordetella pertussis," Molecular Biology, 1991, vol. 5 (7):1649-1656.
De Filette et al.: "Improved design and intranasal delivery of an M2e-based human influenza A vaccine," Vaccine, 2006, vol. 24, pp. 6597-6691.
Laemmli, U.K.: "Cleavage of Structural Proteins during the Assembly of the Head of Bacteriophage T4," Nature, 1970, pp. 680-685.
Humbert, Marc et al.: "Elevated expression of messenger ribonucleic acid encoding IL-13 in the bronchial mucosa of atopic and nonatopic subjects with asthma," Journal of Allergy and Clinical Immunology, 1997, vol. 99 (5):657-665.
Huang, Chin Chiang, et al.: "Experimental Whooping Cough," N Engl J Med, 1962, vol. 266:105-111.
Holgate, Stephen, et al.: "The anti-inflammatory effects of omalizumab confirm the central role of IgE in allergic inflammation," J Allergy Clin Immunol, 2005, vol. 115:459-465.
Hausman, Sally Z. and Drusilla L. Burns: Use of Pertussis Toxin Encoded by ptx Genes from Bordetella bronchiseptica to Model the Effects of Antigenic Drift of Pertussis Toxin on Antibody Neutralization, Infection and Immunity, 2000, vol. 68, No. 6:3763-3767.
Hansen, Gesine et al.: "Allergen-specific Th1 cells fail to counterbalance Th2 cell-induced airway hyperreactivity but cause severe airway inflammation," J. Clin. Invest., 1999, vol. 103:175-183.
Hamelmann, E. et al.: "Role of IgE in the development of allergic airway inflammation and airway hyperresponsiveness a murine model," Allergy, 1999, vol. 54:297-305.
Gleich, Gerald J.: "Mechanisms of eosinophil-associated inflammation," J. Allergy Clin. Immunol., 2000, pp. 651-663.
Giefing, Carmen et al.: "Discovery of a novel class of highly conserved vaccine antigens using genomic scale antigenic fingerprinting of pneumococcus with human antibodies," JEM, 2008, vol. 205(1):117-131.
Galli, Stephen J., et al.: "The development of allergic inflammation," Nature, 2008, vol. 454:445-454.
Zhao, Zhanqin, et al.: "Protecting mice from fatal Bordetella brochiseptica infection by immunization with recombinant pertactin antigens," Acta Microbiologica Sinica, 2008, vol. 48 (3):337-341.
Willems, Rob J.L. et al: "The efficacy of a whole cell pertussis vaccine and fimbriae against Bordetella pertussis and Bordetella parapertussis infections in a respiratory mouse model," Vaccine, 1998, vol. 16 (4) 410-416.
Varga, Steven M. et al: "The Attachment (G) Glycoprotein of Respiratory Syncytial Virus Contains a Single Immunodominant Epitope That Elicits Both Th1 and Th2 CD4+ T Responses," The Journal of Immunology, 2000, vol. 165:6487-6495.
Stibitz, Scott: "Use of conditionally counterselectable suicide vectors for allelic exchange," Methods in Enzymology, 1994, vol. 235:458-465; Abstract.
Stainer, D.W. and M.J. Scholte: "A simple chemically defined medium for the production of phase I Bordetella pertussis," Journal of General Microbiology, 1971, vol. 63:211-220.
Skerry, Ciaran M. and Bernard P. Mahon: "A live, attenuated bordetella pertussis vaccine provides long-term protection against virulent challenge in a murine model," Clinical and Vaccine Immunology, 2011, vol. 18:187-193.
Simon, R. et al: "A broad host range mobilization system for in vivo genetic engineering: transposon mutagenesis in gram negative bacteria," Nature Biotechnology, 1983, vol. 1:784-791.
Reveneau, Nathalie et al: "Tetanus toxin fragment C-specific priming by intranasal infection with recombinant Bordetella pertussis," Vaccine, 2002, vol. 20:926-933.
Renauld-Mongenie, Genevieve, et al: "Induction of mucosal immune responses against a heterologous antigen fused to filamentous hemagglutinin after intranasal immunization with recombinant Bordetella pertussis," Proc. Natl. Acad. Sci., 1996, vol. 93:7944-7949.
Quandt, J. and Michael F. Hynes: "Versatile suicide vectors which allow direct selection for gene replacement in gram-negative bacteria," Gene, 1993, vol. 127 (1):15-21; Abstract.
Power, Ultan F. et al: "Identification and characterisation of multiple linear B cell protectopes in the respiratory syncytial virus G protein," Vaccine, 2001, vol. 19, Issues 17-19:2345-2351; Abstract.
Feunou, Pascal: "T.119.T-but not B-cell-mediated protection induced by nasal administration using live attenuated bordetella pertussis BPZE1 Cross Protect Against B. Parapertussis," Clinical Immunology, 2009, vol. 131, Supplement 1, p. S86; Abstract.
Narasaraju, T. et al: "Adaptation of human influenza H3N2 virus in a mouse peumonitis model: insights into viral virulence, tissue tropism and host pathogenesis," Microbes and Infection 11, 2009:2-11.

(56) References Cited

OTHER PUBLICATIONS

Mutsch, M. et al: Use of the inactivated intranasal influenza vaccine and the risk of Bell's Palsy in Switzerland, The New England Journal of Medicine, 2004, vol. 350:896-903.
Mills, KH et al: "A respiratory challenge model for infection with Bordetella pertussis" application in the assessment of pertussis vaccine potency and in defining the mechanism of protective immunity, Dev Biol Stand, 1998, vol. 95:31-41; Abstract.
Mielcarek, Nathalie et al: "Attenuated bordetella pertussis: new live vaccines for intranasal immunisation," Vaccine, 2006, S2:54-55.
Mielcarek, Nathalie et al: "Intranasal priming with recombinant Bordetella pertussis for the induction of a systemic immune response against a heterologous antigen," Infection and Immunity, 1997:544-550.
Mielcarek, Nathalie et al: "Nasal vaccination using live bacterial vectors," Advanced Drug Delivery Review, 2001, vol. 51:55-69.
Mekseepralard, C. et al: "Protection of mice against human respiratory syncytial virus by wild-type and aglycosyl mouse-human chimaeric IgG antibodies to subgroup-conserved epitopes on the G glycoprotein," Journal of General Virology, 2006, vol. 87:1267-1273.
Menozzi, F.D. et al: "Identification and purification of transferring- and lactoferrin-binding proteins of bordetella pertussis and bordetella bronchiseptica," Infection and Immunity, 1991:3982-3988.
McGuirk, P. et al: "Pathogen-specific T regulatory 1 cells induced in the respiratory tract by a bacterial molecule that stimulates interleukin 10 production by dendritic cells: a novel strategy for evasion of protective T helper type 1 resonses by Bordella pertussis," J.Exp. Med., 2002, vol. 195, No. 2:221-231.
Mascart, Francoise, et al: "Bordetella pertussis infection in 2-month-old infants promotes type 1 T cell responses," The Journal of Immunology, 2003, vol. 170:1504-1509.
Marsolais, David et al: "A critical role for the sphingosine analog AAL-R in dampening the cytokin response during infuenza virus infection," The National Academy of Sciences of the USA, 2009, vol. 106(5):1560-1565.
Feunou, Pascal Feunou et al: "Genetic stability of the live attenuated Bordetella pertussis vaccine candidate BPZE1," Vaccine, 2008, No. 26:5722-5727.
Mielcarek, Nathalie et al: "Live Attenuated B. pertussis as a single-dose nasal vaccine against whooping cough," PLOS Pathogens, 2006, vol. 2, Issue 7:0662-0670.
Gorringe, Andrew R. and Thomas E. Vaughan: "Bordetella pertussis fimbriae (Fim): relevance for vaccines," Expert Reviews Vaccines Early online, 2014:1-10.
Hallander, Hans O. et al: "Should fimbriae be included in pertussis vaccines? Studies on ELISA IgG anti-Fim2/3 antibodies after vaccination and infection," APMIS, 2009, vol. 117, No. 9:660-671.
Debrie, Anne-Sophie et al: "Construction and evaluation of Bordetella pertussis live attenuated vaccine strain BPZE1 producing Fim3," Vaccine, 2018, vol. 36:1345-1352.
Locht, Camille, et al: "Common accessory genes for the Bordetella pertussis filamentous hemagglutinin and fimbriae share sequence similarities with the papC and papD gene families," The EMBO Journal, 1992, vol. 11(9):3175-3183.
Locht, Camille et al: "Bordetalla pertussis, molecular pathogenesis under multiple aspects," Current Opinion in Microbiology, 2001, vol. 4:82-89.
Kashimoto, Takashige, et al: "Identification of functional domains of Bordetella dermonecrotizing toxin," Infect. Immun., 1999, vol. 67(8):3727-3732.
Kavanagh, H. et al: "Attenuated bordetella pertussis vaccine strain BPZE1 modulates allergen-induced immunity and prevents allergic pulmonary pathology in a murine model," Clinical & Experimental Allergy, 2010, vol. 40(933-94.
Ho, Si Ying et al: "Highly attenuated Bordetella pertussis Strain BPZE1 as a potential live vehicle for delivery of heterologous vaccine candidates," Infection and Immunity, 2008, vol. 76:111-119.

Higgins, Sarah C. et al: "Toll-like receptor 4-mediated innate IL-10 activates antigen-specific regulatory T cells and confers resistance to Bordetella pertussis by inhibiting inflammatory pathology," The Journal of Immunology, 2003, vol. 171:3119-3127.
Feunou, Pascal et al: "Genetic stability of the live attenuated Bordetella pertussis vaccine candidate BPZE1," Vaccine, 2008, vol. 28:5722-5727.
Ennis, D.P. et al: "Prior Bordetella pertussis infection modulates allergen priming and the severity of airway pathology in a murine model of allergic asthma," Clin Exp Allergy, 2004, vol. 34:1488-1497.
Ennis, D.P. et al: Whole-cell pertussis vaccine protects against Bordetella pertussis exacerbation of allergic asthma, Immunology Letters 97, 2005, pp. 91-100.
Das, Pam: "Whopping cough makes global comeback," The Lancet Infectious Diseases, 2002, vol. 2:322.
Coppens, Isabelle et al: "Production of Neisseria meningitidis transferrin-binding protein B by recombinant Bordetella pertussis," Infection and Immunity, 2001, pp. 5440-5446.
Child Innovac; European Network on Nasal Vaccination against Respiratory Infections in Young Children, 2008, http://www.ist-world.org/ProjectDetails.aspx?; last accessed on Jan. 6, 2015.
Carbonetti, Nicholas H.: "Immunomodulation in the pathogenesis of Bordetella pertussis infection and disease," Current Opinion in Pharmacology, 2007, vol. 7:272-278.
Antoine, R. and C. Locht: "Roles of the disulfide bond and the carboxy-terminal region of the S1 subunit in the assembly and biosynthesis of pertussis toxin," Infect.Immun., 1990, vol. 56(6):1518-1526.
Alonso, Sylvie et al: "Production of nontypeable haemophilus influenzae HtrA by recombinant Bordetella pertussis with the use of filamentous hemagglutinin as a carrier," Infection and Immunity, 2005, pp. 4295-4301.
Abe, Takayuki et al: "Baculovirus induces an innate immune response and confers protection from lethal influenza virus infection in mice," J Immunol, 2003, vol. 171:1133-1139.
Feunou, Pascal et al: "Long-term immunity against pertussis induced by a single nasal administration of live attenuated B. pertussis BPZE1," Vaccine, 2010, vol. 28:7047-7053.
Mielcarek, Nathalie et al: "Dose Response of attenuated Bordetella pertussis BPZE1-induced protection in mice," Clinical and Vaccine Immunology, 2010, pp. 317-324.
Mielcarek, Nathalie et al: "Live attenuated B. pertussis as a single-dose nasal vaccine against whooping cough," PLoS Pathogens, 2006, vol. 2(7): 662-670.
Renauld-Mongenie, G. et al:Distinct roles of the N-terminal and C-terminal precursor domains in the biogenesis of the Bordetella pertussis filamentous hemagglutinin, J. Bacteriol., 1996, vol. 178(4):1053-1060.
Mattoo, S. et al: "Mechanisms of Bordetella pathogenesis," Frontiers in Bioscience, 2001, vol. 6:168-186.
Mattoo, S. and James D. Cherry: "Molecular pathogenesis, epidemiology, and clinical manifestations of respiratory infections due to Bordetella pertussis and other Bordetella subspecies," Clinical Microbiology Reviews, 2005, vol. 18(2):326-382.
Martignon, G. et al: "Does childhood immunization against infectious diseases protect from the development of atopic disease," Pediatr Allergy Immunol, 2005, vol. 16:193-200.
Locht, Camille et al: "Bordetella pertussis: from functional genomics to intranasal vaccination," Int. J. Med. Microbiol., 2004, vol. 293:583-588.
Harju, T.H. et al: Pathogenic bacteria and viruses in induced sputum or pharyngeal secretions of adults with stable asthma, Thorax, 2006, vol. 61:579-584.
Grueber, C. et al: "Early atopic disease and early childhood immunization—is there a link?," Allergy, 2008, vol. 63:1464-1472.
Gern, James E.: "Viral and bacterial infections in the development and progression of asthma," J Allergy Clin Immunol, 2000, pp. S497-S501.
Ennis, Darren P.: "A cellular pertussis vaccine protects against exacerbation of allergic asthma due to Bordetella pertussis in a murine model," Clin. Diagn. Lab. Immunol., 2005, vol. 12(3):409-417.

(56) References Cited

OTHER PUBLICATIONS

Kim, Young-Suk, et al.: "Inhibition of murine allergic airway disease by Bordetella pertussis," Immunology, 2004, vol. 112:624-630.

Li,R. et al: "Attenuated Bordetella pertussis BPZE1 protects against allergic airway inflammation and contact dermatitis in mouse models," Allergy, 2012, vol. 67:1250-1258.

Grueber, C. et al: "Common vaccine antigens inhibit allergen-induced sensitization and airway hyperresponsiveness in a murine model," Allergy, 2006, vol. 61:820-827.

Feunou, Pascal et al: "T- and B-Cell Mediated Protection Induced by Novel, Live, Attenuated Pertussis Vaccine in Mice. Cross Protection against Parapertussis," PLoS One, Apr. 2010, vol. 5, Issue 4:1-10.

Inatsuka, Carol S. et al: "Pertactin is required for Bordetella species to resist neutrophil-mediated clearance," Infection and Immunity, Jul. 2010, vol. 78, No. 7:2901-2909.

Solans, Luis et al: "The PhoP-dependent ncRNA Mcr7 modulates the TAT secretion system in Mycobacterium tuberculosis," PLOS, May 2014, vol. 10, No. 5:1-17.
Zeddeman, A. et al: "Investigations into the emergence of pertactin-deficient Bordetella pertussis isolates in six European countries, 1996 to 2012," Research Articles, Aug. 21, 2014, pp. 1-11; <<www.eurosurveillance.org>>.
Thorstensson, R. et al: "A Phase I Clinical Study of a Live Attenuated Bordetella pertussis vaccine—BPZE1; A Single Centre, Double-Blind, Placebo-Controlled, Dose-Escalating Study of BPZE1 Given intranasally to healthy adult male volunteers," Plos One, Jan. 2014, vol. 9, No. 1:10.

Stevenson, Andrew and M. Roberts: "Use of Bordetella bronchiseptica and Bordetella pertussis as live vaccines and vectors for heterologous antigens," FEMS Immunology and Medical Microbiology, 2003, vol. 37:121-18.

Burnette, W. Neal et al.: Pertussis Toxin S1 Mutant with Reduced Enzyme Activity and a Conserved Protective Epitope, 1988, Science, vol. 242:72-74.
Li, Rui: "Development of Bordetella Pertussis as a Live Vehicle for Heterologous Antigen Delivery, and its Application as a Universal Influenza A Vaccine," thesis submitted to the National University of Singapore, 2010, pp. 1-258.
Gross, Mary K. et al: "Targeted mutations that ablate either the adenylate cyclase or hemolysin function of the bifunctional cyaA toxin of Bordetella pertussis abolish virulence," Proc. Natl. Acad. Sci. USA, Jun. 1992, vol. 89:4898-4902.
Lim, Annabelle et al: "Protective role of adenylate cyclase in the context of a live pertussis vaccine candidate," Microbes and Infection, 2014, vol. 16:51-60.
Wang, Xianzhe and Jennifer A. Maynard: "The Bordetella Adenylate cyclase repeat-in-toxin (RTX) domain is immunodominant and elicits neutralizing antibodies," The Journal of Biological Chemistry, 2015, vol. 290, No. 6:3576-3591.

* cited by examiner

FIG. 6

SEQUENCE LISTING

```
<160> NUMBER OF SEQ ID NOS: 6

<210> SEQ ID NO 1
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
gagctcttta ccgcggccgc cagttgttca tcaatg                            36

<210> SEQ ID NO 2
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
ggatccatca tcgagaccga ctgg                                         24

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

```
            Synthetic primer"

<400> SEQUENCE: 3 agctagggt agaccacgga                                                    20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
ataactcttc tggcgccaag                                                   20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
catgacggca cccctcagta                                                   20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
ttcacgtacg aggcgagata                                                   20
```

BORDETELLA STRAINS EXPRESSING SEROTYPE 3 FIMBRIAE

CROSS-REFERENCE TO RELATED APPLICATIONS

The present application is a by-pass continuation under 35 U.S.C. 111(a) of international patent application number PCT/EP2018/078522 filed on Oct. 18, 2018 which claims the priority of U.S. provisional patent application Ser. No. 62/574,068 filed on Oct. 18, 2017.

SEQUENCE LISTING

The instant application contains a Sequence Listing which has been submitted electronically in ASCII format and is hereby incorporated by reference in its entirety. Said ASCII copy, created on Oct. 10, 2018, is named 7056-0091_SL and is 1,833 bytes in size.

STATEMENT AS TO FEDERALLY SPONSORED RESEARCH

Not applicable.

FIELD OF THE INVENTION

The invention relates generally to the fields of microbiology, immunology, vaccinology, sero-epidemiology, biochemistry and medicine. More particularly, the invention relates to live attenuated *Bordetella* strains modified to express serotype 3 fimbriae and their use in vaccines.

BACKGROUND

Whooping cough or pertussis is a severe respiratory disease that can be life-threatening, especially in young infants, and its incidence is on the rise in several countries, despite a global vaccination coverage of >85%, according to the World Health Organization. However, it also affects adolescents and adults, where symptoms are usually atypical, and therefore the disease often remains undiagnosed in these age groups. Nevertheless, adolescents and adults, even if they remain asymptomatic, can transmit the causative agent *Bordetella pertussis* to young infants before they are protected by the primary vaccination series. In fact, a recent wavelet analysis of *B. pertussis* infection in the US and the UK, combined with a phylodynamic analysis of clinical isolates showed that asymptomatic transmission is the principle cause of the recent pertussis resurgence. In addition, asymptomatic *B. pertussis* infection may not be anodyne, as epidemiological evidence suggests that *B. pertussis* infection may be related to auto-immune diseases, such as Celiac disease, multiple sclerosis, and even Alzheimer's disease Currently available whole-cell or acellular vaccines have been very effective in reducing the incidence of whooping cough after three primary vaccination doses. However, in contrast to prior infection with *B. pertussis*, they are much less effective in reducing asymptomatic colonization, as shown in the recently established baboon model. Although vaccinated baboons were protected against pertussis disease upon experimental infection with *B. pertussis*, they could readily be infected and transmit the organism to littermates, even in the absence of symptoms, in contrast to convalescent baboons. Altogether these observations illustrate the shortcomings of currently available vaccines, and call for new vaccines that protect both against disease and infection.

Based on the observation that the best way to protect against *B. pertussis* colonization is prior infection, a live attenuated vaccine has been developed that can be administered by the nasal route, in order to mimic as much as possible natural infection without causing disease. The vaccine strain, called BPZE1, lacks the gene coding for dermonecrotic toxin, produces genetically detoxified pertussis toxin and is deficient for tracheal cytotoxin production by the replacement of the *B. pertussis* ampG gene with the *Escherichia coli* ampG gene. BPZE1 has been shown to be safe in pre-clinical models, including in severely immunocompromised mice, and to be genetically stable after serial passages in vitro and in vivo for at least 12 months. It protects mice against *B. pertussis* challenge after a single nasal administration, both via protective CD4+ T cells and antibodies, and protection was shown to be long lived after a single nasal vaccination. It also has recently been shown to reduce nasopharyngeal infection by *B. pertussis* in baboons by 99.992% compared to non-vaccinated baboons. BPZE1 has now successfully completed a first-in-man phase I clinical trial and was found to be safe in human adults, able to transiently colonize the human nasopharynx and to induce immune responses to all tested antigens in all colonized individuals.

*B. pertussis* produces two serologically distinct fimbriae, composed of either Fim2 or Fim3 as the major fimbrial subunit. These fimbriae are involved in the attachment of the bacteria to respiratory epithelial cells. While BPZE1 produces only Fim2, it also produces hundreds of other antigens (e.g., pertussis toxin, FHA, and pertactin). It thus has been shown to induce significant protection against a wide array of *B. pertussis* clinical isolates, including those, which only produce Fim3.

SUMMARY

Described herein is the development of BPZE1f3, deposited with the Collection Nationale de Cultures de Microorganismes (CNCM, Institut Pasteur, 25 rue du Docteur Roux, F-75724 Paris Cedex 15, FRANCE) on Oct. 11, 2017 under registration number CNCM I-5247, a *B. pertussis* strain derived from BPZE1 that produces both serotype 2 fimbriae (Fim2) and serotype 3 fimbriae (Fim3). Given that BPZE1 produces several hundred different non-fimbriae antigens that could be targeted by immune responses, adding a single new antigen was not expected to have much effect on the protective effect of the bacteria. It was thus surprisingly discovered that vaccination with BPZE1f3 significantly improved the protective effect against certain clinical isolates which produce Fim3 and not Fim2.

In the study described in the Examples section below, an intranasal mouse challenge model was used to examine the protective potential of Fim2-producing BPZE1 and Fim2-,3-producing BPZE1f3 to protect against clinical isolates of different serotypes. Both vaccine strains appeared to induce significant protection against all examined clinical isolates. However, BPZE1f3 provided significantly better protection than BPZE1 against a clinical isolate that only produced Fim3, confirming sero-specific protection to a certain degree.

A number of Fim2 and Fim3 subtypes have been identified. These include two Fim2 subtypes, Fim2-1, Fim2-2, which vary from each other by a single amino acid difference. Fim2-1 carries an arginine at position 174, whereas this is changed to a lysine in Fim2-2. The Fim3 subtypes are encoded by 6 different alleles. Fim3-2 differs from Fim3-1 by a single amino acid substitution at position 87: Alanine and Glutamate for Fim3-1 and Fim3-2, respectively. Fim3-3 carries, in addition to the Glutamate substitution at position 87, a change from Threonine in Fim3-1 to Alanine in Fim3-3. The fim3-4 allele differs from fim3-1 only by a single silent nucleotide polymorphism, whereas the other five alleles vary by three codons, each leading to one amino acid change in the major fimbrial subunit. Given the minor sequence differences between the various subtypes, it is likely that BPZE1f3 is protective against all of them.

To induce immune responses to fimbrial antigens, production of these antigens must be sufficiently stable in live *B. pertussis* vaccine strains. The stability of the Fim2 and Fim3 production deserves particular attention, since phase variation from one serotype to another has been described, especially during infection, and can be driven by vaccine pressure. This phase transition from high to low fimbrial production depends on the number of cytosines present in a C-string within the fim promoter region. The number of cytosines within this C-string may affect the distance between the −10 box of the fim promoters and the binding site of BvgA, the transcriptional activator required for the expression of fim and other *B. pertussis* virulence genes. It has long been known that DNA regions with repeated base pairs sequences, predominantly in C-strings, are particularly prone to additions or deletions of a single base. Since BPZE1f3 was constructed by the addition of a single C:G base pair in a stretch of 13 C in the promoter region to allow for fim3 expression, it was thought that the fim3 expression would be unstable. Unexpectedly, however, after several passages of BPZE1f3 through mice, 100% of the bacteria recovered after the first passage remained Fim3+, as well as Fim2+. During subsequent passages (up to 3), close to 90% of the bacteria still expressed both fim3 and fim2, indicating that fim expression was sufficiently stable to induce serotype-specific immunity, as confirmed by the protective effect of BPZE1f3 against Fim3-only producing clinical isolates.

Accordingly, described herein is a live attenuated *Bordetella* strain engineered to stably produce Fim3, wherein the live attenuated *Bordetella* strain retains the ability to colonize a mammalian subject's lungs and induce a protective immune response against *Bordetella* infection (e.g., the *Bordetella* strain designated BPZE1f3). The live attenuated *Bordetella* strain can be one that also stably produces Fim2. The live attenuated *Bordetella* strains described herein can also be rendered deficient in at least one (1, 2, or 3) of \ the following virulence factors: a functional pertussis toxin (PTX), a functional dermonecrotic toxin (DNT), and a functional tracheal cytotoxin (TCT).

Also described herein are vaccines that include a live attenuated *Bordetella* strain engineered to stably produce Fim3 mentioned herein and a pharmaceutically acceptable carrier. The vaccine can be provided in a single dosage form which includes at least $1 \times 10^6$ (e.g., at least $1 \times 10^6$, $5 \times 10^6$, or $1 \times 10^7$) colony forming units (CFU) of the strain.

Further described herein are methods of protecting a mammalian subject (e.g., a human being) from developing pertussis, which include the step of administering to the mammalian subject a vaccine including a pharmaceutically acceptable carrier and a live attenuated *Bordetella* strain engineered to stably produce Fim3, wherein the live attenuated *Bordetella* strain retains the ability to colonize a mammalian subject's lungs and induce a protective immune response against *Bordetella* infection.

As used herein, a bacterial strain that "stably produces" an antigen is one that can be passaged at least once (e.g., 1, 2, 3, 4, 5 or more times) through a host animal without losing more than 50% (or more than 60, 70, 80, 90, 95, 97, 98, or 99%) of the expression of that antigen. For example, an isolated *Bordetella* bacterial strain engineered to stably produce Fim3 is one that has been genetically modified to express Fim3, and retain at least 50% (e.g., 50, 60, 70, 80, 90, 95, 97, 98, or 99%) of the expression of Fim-3 after being passaged through a mouse, e.g., by the methods described in the Examples section below.

Reference to a "functional" virulence factor means that a bacterial strain possesses at least 50% of the enzymatic activity of that virulence factor compared to a the wild-type version of that virulence factor. A bacterial strain that "has been rendered deficient in at least one virulence factor" is a strain engineered to express less than 70, 80, 90, 95, 96, 97, 98, or 99% of the enzymatic or functional activity of that virulence factor as compared to the parent strain from which is was derived.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patents, and patent applications mentioned herein are incorporated by reference in their entirety. In the case of conflict, the present specification, including definitions will control. In addition, the particular embodiments discussed below are illustrative only and not intended to be limiting.

DESCRIPTION OF THE DRAWINGS

FIG. 6 is a graph showing the stability of Fim2 and Fim3 production by BPZE1f3, where BPZE1f3 was passaged three times in mice, and at each passage (P1 to P3), 94 colonies were analysed by whole-cell ELISA for the presence of Fim2 (white bars) and Fim3 (black bars) using anti-Fim2 and anti-Fim3 monoclonal antibodies.

DETAILED DESCRIPTION

Figure 1A:
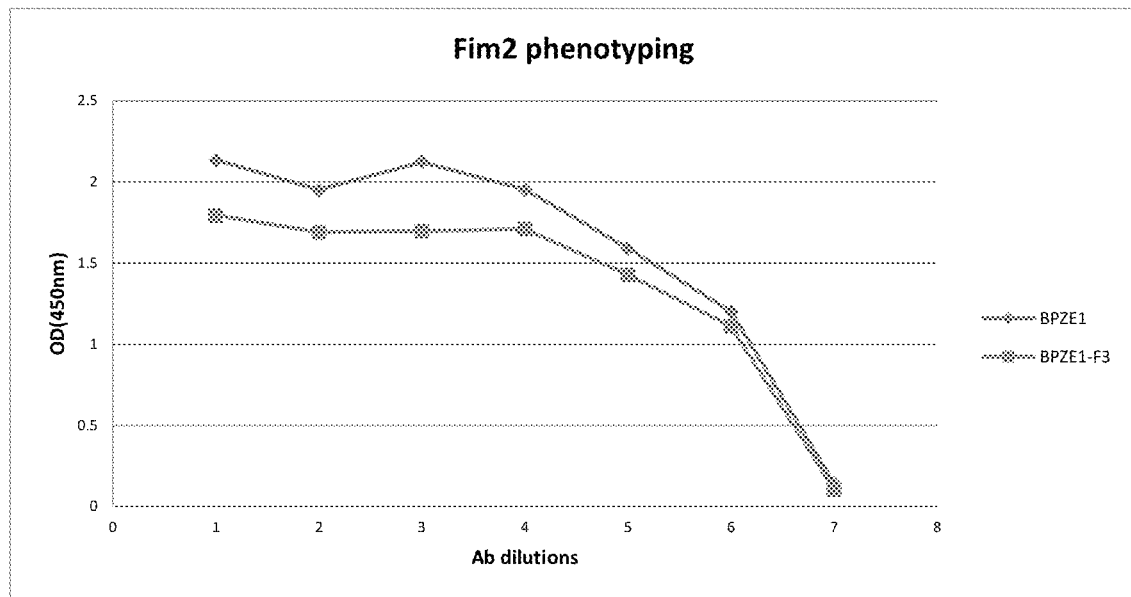
FIG. 1A is a graph showing the production of Fim2 by BPZE1 (in diamonds) and BPZE1f3 (in squares).
Figure 1B:
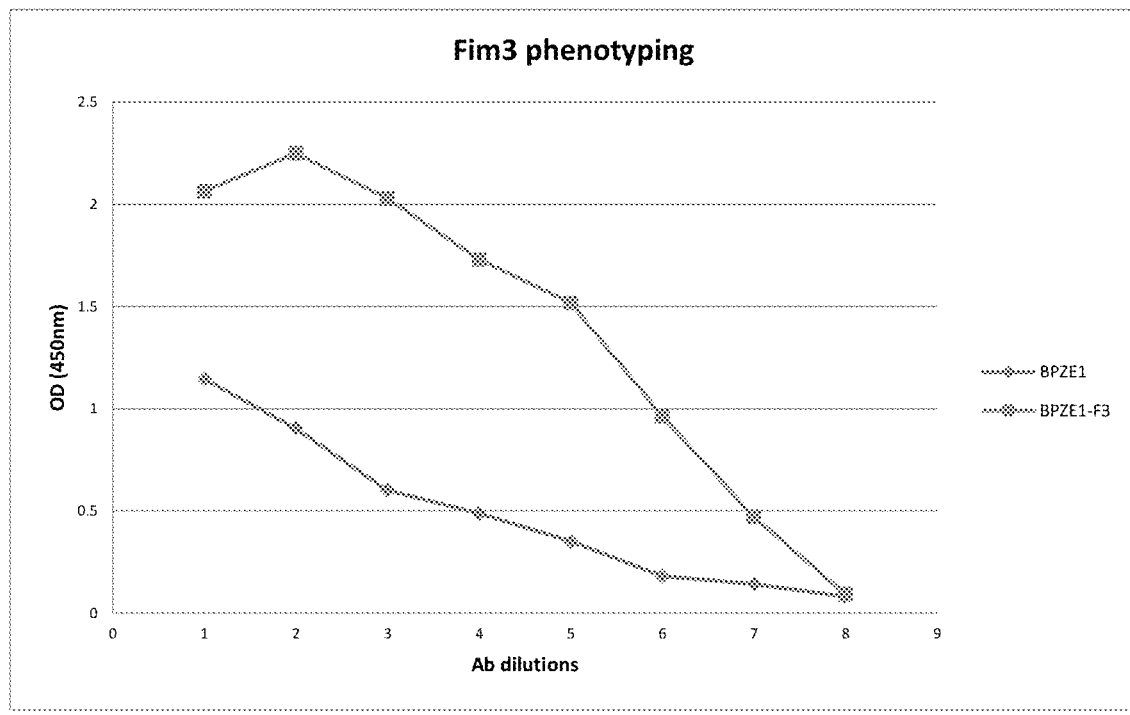
FIG. 1B is a graph showing the production of Fim3 by BPZE1 (in diamonds) and BPZE1f3 (in squares).
Figure 2A:
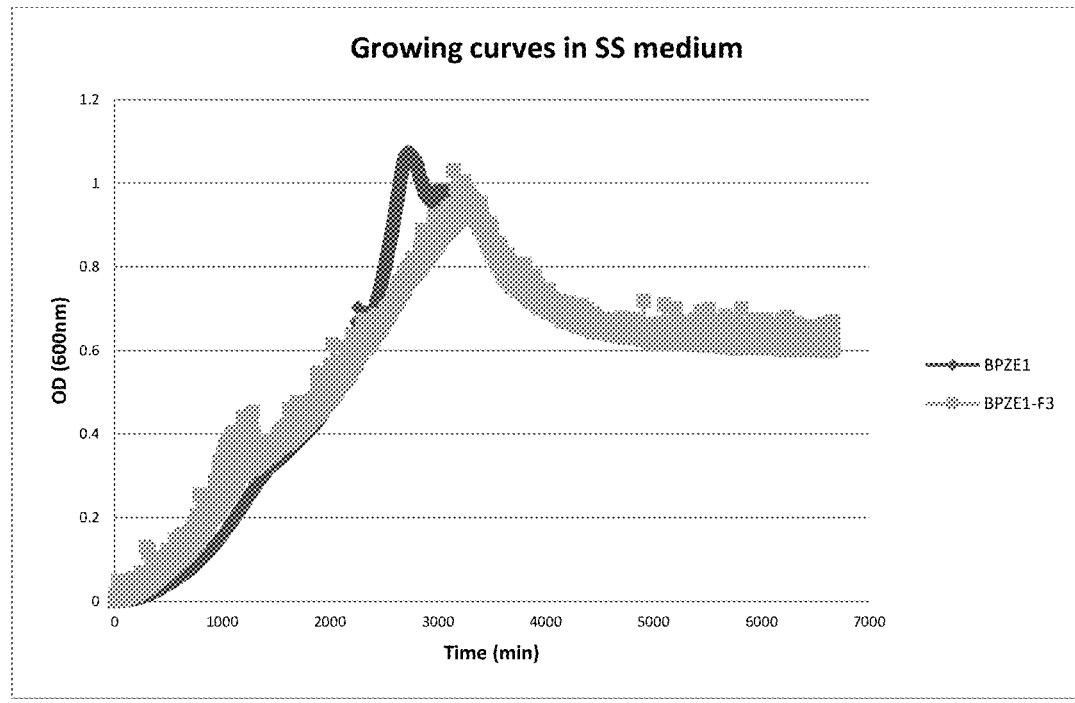
FIG. 2A is a graph showing the in vitro growth of BPZE1 (in diamonds) and BPZE1f3 (in squares) in modified Stainer-Scholte medium.
Figure 2B:
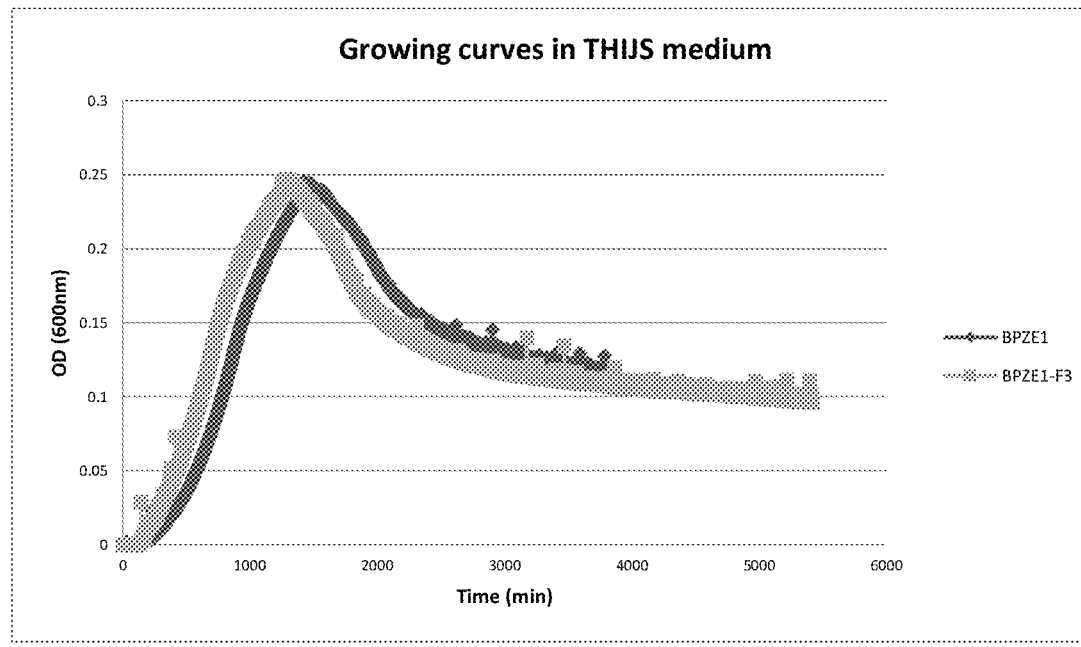
FIG. 2B is a graph showing the in vitro growth of BPZE1 (in diamonds) and BPZE1f3 (in squares) in fully synthetic Thijs medium.
Figure 3:
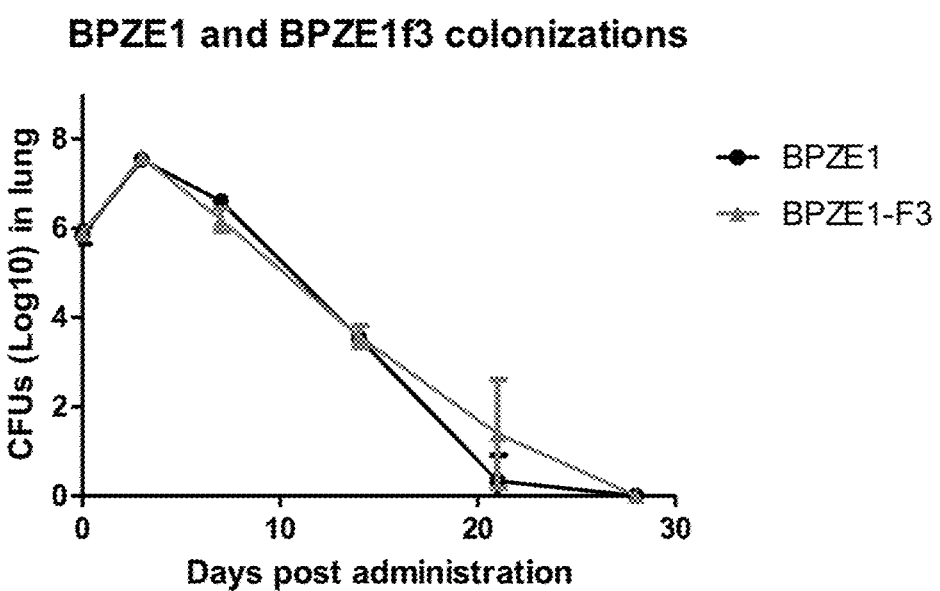
FIG. 3 is a graph showing lung colonization of mice nasally inoculated with $10^6$ CFU of BPZE1 (in black) or BPZE1f3 (in grey), where the bacterial loads in the lungs were measured at the indicated time points.
Figure 4A:
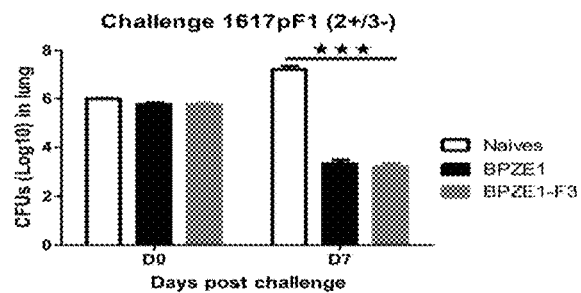
FIGS. 4A-4E represent a series of graphs showing BPZE1- and BPZE1f3-induced protection against clinical *B. pertussis* isolates where mice received nasally either $10^5$ CFU of BPZE1 (black bars) or BPZE1f3 (grey bars), or were left untreated (white bars). Four weeks after vaccination the mice were challenged with $10^6$ CFU of 1617pF1 (A), 403pF1 (B), P134 (C), 1412pF1 (D) or 403pF3 (E). Three h (left part of the panels, DO) or 7 days (right part of the panels, D7) after challenge, the bacterial loads in the lungs were measured and are presented as means and standard deviations of CFU. Three (for DO) or five (for D7) mice per group were used. ***, $p<0.001$.
Figure 4B:
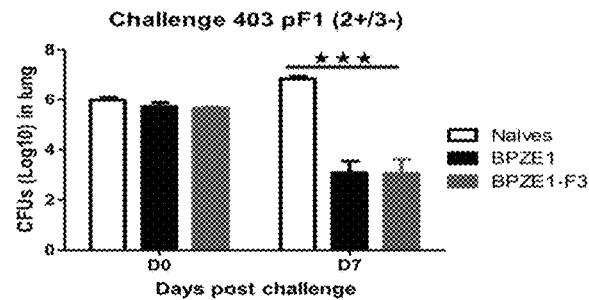
Figure 4C:
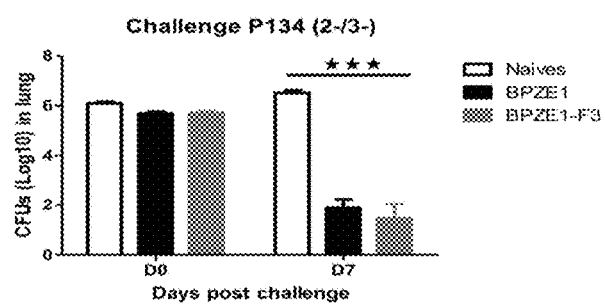
Figure 4D:
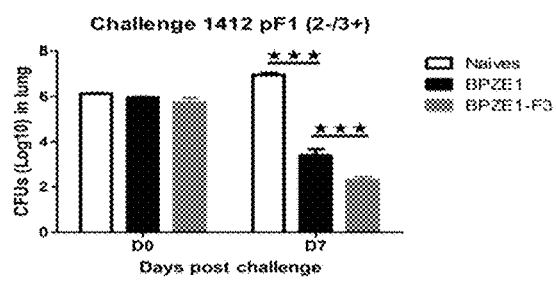
Figure 4E:
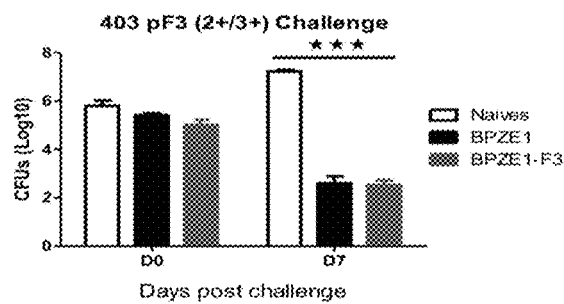

Described herein is a Fim3-producing BPZE1 derivative with sufficiently stable fim3 expression to provide improved protection in mice against Fim3-only producing clinical *B. pertussis* isolates. The fim3 expression in BPZE1f3 did not alter the protective efficacy against Fim2+ strains, nor against strains that produce neither Fim2 nor Fim3. The below described embodiments illustrate representative examples of these methods. Nonetheless, from the description of these embodiments, other aspects of the invention can be made and/or practiced based on the description provided below.

General Methodology

Methods involving conventional microbiological, immunological, molecular biological, and medical techniques are described herein. Microbiological methods are described in Methods for General and Molecular Microbiology (3d Ed), Reddy et al., ed., ASM Press. Immunological methods are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. General methods of medical treatment are described in McPhee and Papadakis, Current Medical Diagnosis and Treatment 2010, 49th Edition, McGraw-Hill Medical, 2010; and Fauci et al., Harrison's Principles of Internal Medicine, 17th Edition, McGraw-Hill Professional, 2008.

Fim3-Producing *Bordetella* Strains

*Bordetella* species (e.g., *Bordetella pertussis*, *Bordetella parapertussis*, and *Bordetella bronchiseptica*) that lack Fim3 expression can be engineered to produce Fim3 (e.g., Fim3-1, Fim3-2, Fim3-3, or Fim3-4), and otherwise attenuated as described below. These Fim3-producing bacteria might be used to treat and/or prevent symptomatic or asymptomatic respiratory tract infections caused by *Bordetella* species as well as other conditions where BPZE1 was shown to be effective (e.g., allergy and asthma). *Bordetella* strains engineered to produce Fim3 might also be used to prevent transmission of *Bordetella* infections. Attenuated, Fim2-/Fim3-producing *Bordetella pertussis* is preferred for use in human subjects. *Bordetella* strains for use in making Fim3-producing bacteria can be isolated from natural sources (e.g., colonized subjects) or obtained from various culture collections. *Bordetella* strains that have been engineered to produce Fim3 can be made by the methods described below.

Because insufficient attenuation of a pathogenic strain of *Bordetella* might cause a pathological infection in a subject, it is preferred that the *Bordetella* strain engineered to produce Fim3 have lower levels of other virulence factors. On the other hand, to ensure that the Fim3-producing *Bordetella* strains are able to colonize a subject and exert a protective effect on respiratory tract inflammation, it must not be overly attenuated. Attenuation might be achieved by mutating the strain to reduce its production of one or more (e.g., 1, 2, 3, 4, 5 or more) of the following: pertussis toxin (PTX), dermonecrotic toxin (DNT), tracheal cytotoxin (TCT), adenylate cyclase (AC), lipopolysaccharide (LPS), filamentous hemagglutinin (FHA), pertactin, or any of the bvg-regulated components. Methods for making such mutants are described herein and in U.S. Pat. No. 9,119,804 and U.S. patent application Ser. No. 15/472,436. In the experiments presented below, a *Bordetella* strain was engineered to produce Fim 3 that was deficient in DNT and TCT and produced genetically inactive PTX. It was able to colonize the respiratory tract of and induce a protective immune response in, subjects.

Formulations/Dosage/Administration

The *Bordetella* strains engineered to produce Fim 3 can be formulated as a vaccine for administration to a subject. A suitable number of live bacteria are mixed with a pharmaceutically suitable excipient or carrier such as phosphate buffered saline solutions, distilled water, emulsions such as an oil/water emulsions, various types of wetting agents sterile solutions and the like. In some cases the vaccine can be lyophilized and then reconstituted prior to administration. The use of pharmaceutically suitable excipients or carriers which are compatible with mucosal (particularly nasal, bronchial, or lung) administration are preferred for the purpose of colonizing the respiratory tract. See Remington's Pharmaceutical Sciences, a standard text in this field, and in USP/NF.

When formulated for mucosal administration, each dose of the vaccine can include a sufficient number of live *Bordetella* bacteria to result in colonization of the respiratory tract, e.g., approximately (i.e., +/−50%) $5\times10^3$ to $5\times10^9$ bacteria, depending on the weight and age of the mammal receiving it. For administration to human subjects, the dose can include approximately $1\times10^6$, $5\times10^6$, $1\times10^7$, $5\times10^7$, $1\times10^8$, $5\times10^8$, $1\times10^9$, $5\times10^9$, or $1\times10^{10}$ live Fim3-producing *Bordetella* bacteria. The dose may be given once or on multiple (2, 3, 4, 5, 6, 7, 8 or more) occasions at intervals of 1, 2, 3, 4, 5, or 6 days or 1, 2, 3, 4, 5, or 6 weeks, or 1, 2, 3, 4, 5, 6, or 12 months. Generally, sufficient amounts of the vaccine are administered to result in colonization and the protective response. Additional amounts are administered after the induced protective response wanes.

Methods of Eliciting Immune Responses to Protect Against Pertussis

The vaccines described herein can be administered to a mammalian subject (e.g., a human being, a human child or neonate, a human adult, a human being at high risk from developing complications from pertussis, a human being with lung disease, and a human being that is or will become immunosuppressed) by any suitable method that deposits the bacteria within the vaccine in the respiratory tract. For example, the vaccines may be administered by inhalation or intranasal introduction, e.g., using an inhaler, a syringe, an insufflator, a spraying device, etc. While administration of a single dose of between $1\times10^4$ to $1\times10^7$ (e.g., $1\times10^4$, $5\times10^4$, $1\times10^5$, $5\times10^5$, $1\times10^6$, $5\times10^6$, or $1\times10^7$ +/−10, 20, 30, 40, 50, 60, 70, 80, or 90%) live bacteria is typically sufficient to induce protective immunity against developing a *Bordetella* infection such as pertussis, one or more (1, 2, 3, 4, or more) additional doses might be administered in intervals of 4 or more days (e.g., 4, 5, 6, or 7 days; or 1, 2 3, 4, 5, 6, 7, or 8 weeks) until a sufficiently protective immune response has developed. The development of a protective immune response can be evaluated by methods known in the art such as quantifying *Bordetella*-specific antibody titers and measuring of *Bordetella* antigen-specific T cells responses (e.g., using an ELISPOT assay). In cases were a vaccine-induced protective immune response has waned (e.g., after 1, 2, 3, 4, 5, 10 or more years from the last vaccination) a subject may again be administered the vaccine in order to boost the anti-*Bordetella* immune response.

EXAMPLES

Materials and Methods

Culture Conditions

All *B. pertussis* strains were grown on Bordet Gengou (BG) agar with 10% (v/v) sheep blood, in modified Stainer Scholte (SS) medium under agitation as described (Imaizumi et al., Infect Immun 1983; 41:1138-43) or in fully synthetic Thijs medium (Thalen et al., J Biotechnol 1999; 75:147-59). The media were supplemented with the appropriate antibiotics (100 ug/ml of streptomycin or 10 ug/ml of gentamycin for the strains carrying pFUS2 BctA1).

Bacterial Strains

*B. pertussis* BPSM and BPZE1, as well as *Bordetella parapertussis* used in this study have been described previously (Mielcarek et al., PLoS Pathog 2006; 2:e65; Menozzi et al., Infect Immun 1994; 62:769-78). *B. pertussis* strains B0403, B1412, B1617 and B0005 (strain 134 Pillmer) came from the RIVM collection (Bilthoven, The Netherlands). For counter-selection purposes some of the clinical isolates strains were electroporated with the pFUS2 BctA1 suicide plasmid to acquire the gentamycin resistance as described in Antoine et al. (J Mol Biol 2005; 351:799-809). Gentamycin-resistant derivatives after electroporation were checked by PCR to verify the site of insertion of the pFUS2 BctA1 vector into the chromosomal DNA and by ELISA to check the level of surface exposed Fim2 and/or Fim3, as described below. Strain P134S was obtained by selecting a streptomycin derivative of *B. pertussis* B0005. Strain P134S carries, in addition to streptomycin resistance mediated by a mutation in the rpsl gene, a mutation in the fimC gene leading to the loss of the fimbriae production. *Escherichia coli* SM10 (Simon et al., Bio/Technology 1983; 1:784-91) was used for conjugation of the various plasmid constructs into *B. pertussis.*

Construction of the Fim3-positive BPZE1-derivative BPZE1f3

To construct BPZE1f3, the 13 C stretch located in the promoter region of the fim3 gene of BPZE1, 75 bp upstream of the fim3 ATG codon, was replaced by a 14 C stretch in order to trigger the transcription of fim3. The whole fim3 locus, containing the promoter region, was first deleted in the parental strain and then replaced by a fim3 locus with a 14 C stretch. A 2265-bp PCR fragment encompassing the locus was amplified by using the following oligonucleotides (SPfim3UP2: GAGCTCTTTACCGCGGCCGCCAGTTG-TTCATCAATG (SEQ ID NO: 1) and ASPfim3LO2: GGATCCATCATCGAGACCGACTGG (SEQ ID NO: 2)) and cloned into the SacI and BamHI restriction sites of a pBluescript II SK+ plasmid (Addgene). From resulting plasmid, a 904-bp fragment containing the whole locus was removed by SphI restriction to obtain pSKfim3UPLO. The 1351-bp SacI-BamHI fragment of pSKfim3UPLO was inserted into the SacI and BamHI sites of pJQ200mp18rpsL (Antoine, J. Mol. Biol. (2005) 351, 799-809). The recombinant plasmid was then used for double homologous recombination in BPZE1 using conjugation as described previously (Mielcarek et al., PLoS Pathog 2006; 2:e65). The transconjugants were checked for deletion of the whole fim3 locus by PCR using oligonucleotides SPfim3UP2 and ASPfim3LO2. Reintroducing the whole fim3 locus with the 14 C stretch in the promoter was done as follows. A 911-bp synthetic gene encompassing the whole locus with the 14 C stretch was synthesized by GeneArt® Gene Synthesis (ThermoFisher SCIENTIFIC). SphI sites at the extremities of the synthetic fragment were used to insert it into the SphI site of pSKfim3UPLO giving rise to pSKfim3+. The correct orientation of the insert was checked by restrictions. The 2256-bp SacI-BamHI fragment of this plasmid was transferred into the same restriction sites of pJQ200mp18rpsL leading to pJQfim3+. This plasmid was used to do the double homologous recombination to obtain BPZE1f3. The recombinant strain was verified by PCR using oligonucleotides SPfim3UP2 and ASPfim3LO2.

Analysis of Fim2 and Fim3 Production

The *B. pertussis* strains were first inactivated by heating at 56° C. for 30 minutes. The heat-inactivated strains were then coated at an optical density (OD) 600 nm of 0.075 in 96-well plates (Nunc Maxi Sorp,) and incubated overnight at 37° C. until the wells were dry. The wells were then blocked with 100 μl of PBS Tween 0.1% (PBST), containing 1% of Bovine Serum Albumin (BSA). Fim2 and Fim3 monoclonal antibodies (NIBSC, 04/154 and 04/156, respectively) were added in serial dilutions from 1/50 to 1/36450 in PBST (v/v). After three washes, the plates were incubated with 100 μl of horseradish-peroxidase-labeled goat anti-mouse IgG (Southern Biotech) in PBST. Following five washes, the plates were incubated with 100 μl of HRP Substrate TMB solution (Interchim) for 30 min at room temperature. The reaction was stopped by the addition of 50 μl of 1 M $H_3PO_4$. The OD was measured with a Biokinetic reader EL/340 microplate at 450 nm.

DNA Sequencing

PCR amplification of chromosomal DNA was performed using Phusion High-Fidelity DNA Polymerase (Thermofisher) or KAPA HiFi DNA Polymerase (Kapa Biosystems) according to the manufacturer's instructions. The PCR fragments were purified with a QiaQuick PCR purification kit (Qiagen) and sequenced with the primers used for amplification. Primers ptxP Up and ptxP Low used for PCR amplification of ptxP have been described previously (Mooi et al., Emerg Infect Dis 2009; 15:1206-13). Primers prn AF and prn AR used for partial PCR amplification of prn has been described previously (Mooi et al., Infect Immun 1998; 66:670-5). Primers fim2 Up 5'-AGCTAGGGGTAGAC-CACGGA-3' (SEQ ID NO: 3) and fim2 Low 5'-ATAACTCTTCTGGCGCCAAG-3' (SEQ ID NO: 4) were used for amplification and sequencing of fim2. Primers fim3 Up 5'-CATGACGGCACCCCTCAGTA-3' (SEQ ID NO: 5) and fim3 Low 5'-TTCACGTACGAGGCGAGATA-3' (SEQ ID NO: 6) were used for amplification and sequencing of fim3.

Mouse Infection Experiments

BALB/c mice were obtained from Charles River (l'Abresle, France) and maintained under specific pathogen-free conditions in the animal facilities of the Institut Pasteur de Lille. Six week-old BALB/c mice were lightly sedated by intraperitoneal injection with an anesthetic cocktail (ketamine+atropine+valium) before intranasal (i.n.) administration with 20 µl PBS containing $10^6$ colony-forming units (CFU) of *B. pertussis* BPZE1 or BPZE1f3, as previously described (Mielcarek et al., PLoS Pathog 2006; 2:e65). Three mice per group were sacrificed at selected time points after i.n. administration, and their lungs were harvested, homogenized in PBS and plated in serial dilutions onto BG-blood agar to count CFUs after incubation at 37° C. for three to four days.

Mouse Protection Experiments

Six week-old BALB/c mice were i.n. vaccinated with $10^5$ CFU of *B. pertussis* BPZE1 or BPZE1f3, as described above. Four weeks later, naïve and vaccinated mice were challenged with $10^6$ CFU of *B. pertussis* BPSM, the indicated clinical *B. pertussis* isolates or *B. parapertussis* in 20 µl of PBS. Lung colonization was determined 3 h and 7 days later with 3 and 5 mice per group, respectively.

Stability of Fim3 and Fim2 Production $10^6$ CFUs of BPZE1f3 were administered to a sedated mouse in 200 of PBS. 14 days later, the lung was harvested, homogenized and plated onto BG agar. 3-4 days later, 94 individual colonies were inoculated into a 96-well plate containing 100 µl of PBS/well. Control wells contained BPZE1, as a negative control, and BPZE1f3 as a positive control. The amount of bacteria present in each well was determined by OD measurement at 630 nm. After drying, the presence of Fim3 and of Fim2 was evaluated by whole-cell ELISA as described above. After a blocking step with 100 µl PBST containing 1% BSA, bacteria were incubated during one hour with the anti-Fim3 monoclonal antibody 04/156 or anti-Fim2 monoclonal antibody 04/154 at a 1/1350 dilution in 100 µl PBST. After washes and incubation with 100 µl of horseradish-peroxidase-labeled goat anti-mouse IgG (Southern Biotech) in PBST, the presence of Fim3 or Fim2 was evaluated with 100 µl of HRP Substrate TMB solution (Interchim) revelation. The reaction was stopped by the addition of 50 µl of 1 M $H_3PO_4$. The OD was measured with a Biokinetic reader EL/340 microplate at 450 nm.

Results

Construction of BPZE1f3.

In order to construct a BPZE1 derivative that produces Fim3, the fim3 gene was first deleted from BPZE1. The upstream and downstream flanking regions of fim3 were amplified by PCR using the BPZE1 chromosomal DNA as template and were spliced together in the non-replicative vector pJQ200mp 18rpsL (Antoine, J. Mol. Biol. (2005) 351, 799-809). The fim3 gene of BPZE1 was then deleted by allelic exchange after conjugation with *E. coli* SM10 containing the recombinant plasmid. The resulting strain BPZE1Δfim3 was used to re-integrate the fim3 gene together with a functional promoter into the original fim3 locus. The 13-C stretch of the original promoter was replaced by a 14-C stretch, allowing for fim3 expression and inserted into pSKfim3UPLO together with the fim3 open reading frame. The resulting plasmid pJQFim3+ was conjugated into BPZE1Δfim3 via conjugation with *E. coli* SM10: pJQFim3+. This resulted in BPZE1f3.

The production of Fim2 and Fim3 in BPZE1f3 was analyzed by whole-cell ELISA using Fim2-specific and Fim3-specific monoclonal antibodies, respectively. As shown in FIG. 1A, both BPZE1 and BPZE1f3 produced equivalent amounts of Fim2. In contrast, Fim3 was only produced by BPZE1f3, and only background absorbency was detected with the Fim3-specific antibody on whole BPZE1 extracts (FIG. 1B). Both strains grew equally well in Stainer Scholte medium and in the completely synthetic Thijs medium (FIG. 2), indicating that the production of Fim3 did not affect the growth characteristics of BPZE1f3.

Mouse Colonization by BPZE1f3.

To assess the potential role of Fim3 production by BPZE1f3 in the colonization of the mouse respiratory tract, adult mice were infected with $10^6$ CFU of either BPZE1 or BPZE1f3, and 3 mice per group were sacrificed at days 3, 7, 14, 21 and 28 post-infection to quantify the bacterial loads in their lungs. As shown in FIG. 3, the capacity to colonize the mouse lungs was identical between the two strains at all time points analyzed, indicating that the production of Fim3 did not enhance, nor hamper the ability of BPZE1 to colonize the murine respiratory tract.

BPZE1- and BPZE1f3-mediated protection against clinical *B. pertussis* isolates.

To examine the relative protective effects of BPZE1 and BPZE1f3 against clinical isolates that differ with respect to their production of Fim2 and Fim3, we used a sub-optimal immunization protocol, in which mice were intranasally immunized with $10^5$ CFU of the vaccine strains and infected one month later with $10^6$ CFU of the challenge strains. This protocol was used because it is best suited to detect potential differences between vaccine lots, as the standard vaccination protocol using $10^6$ CFU of the vaccine strain followed two months later by infection with $10^6$ CFU of the challenge strain usually results in total clearance 7 days after challenge.

The potency of the two vaccine strains was tested against four different clinical isolates from the *B. pertussis* culture collection of the RIVM (Bilthoven, The Netherlands). The five strains had the following characteristics with respect to Fim2 and Fim3 production: 1617F1 (Fim2+Fim3-), 403pF1 (Fim2+Fim3-), P134 (Fim2-Fim3-), 1412pF1 (Fim2-Fim3+) and 403pF3 (Fim2+Fim3+). The genomic key features of these strains are presented in table I below. After vaccination and challenge infection the bacterial load of the challenge strain was measured in the lungs 3 h and 7 days after infection.

TABLE I

Key genomic features of the *B. pertussis* strains.

| | Pptx[1] | fim2 | fim3 | serotype | Prn[3] | ptx-s1[4] |
|---|---|---|---|---|---|---|
| BPSM | P1 | fim2-1[2] | fim3-1[2] | 2+/3− | prn-1 | ptxA2 |
| BPZE1 | P1 | fim2-1 | fim3-1 | 2+/3− | prn-1 | ptxA2 (R9K, E129G) |
| BPZE1f3 | P1 | fim2-1 | fim3-1 | 2+/3+ | prn-1 | ptxA2 (R9K, E129G) |
| B1412 pF1 | P1 | fim2-1 | fim3-1 | 2−/3+ | prn-1 | ptxA1 |
| B1617 pF1 | P1 | fim2-1 | fim3-1 | 2+/3− | prn-1 | ptxA1 |
| B0403 pF1 | P1 | fim2-1 | fim3-1 | 2+/3− | prn-1 | ptxA2 |
| B0403 pF3 | P1 | fim2-1 | fim3-1 | 2+/3+ | prn-1 | ptxA2 |
| P134S | P1 | fim2-1 | fim3-1 | 2−/3− | prn-1 | ptxA2 |

[1]Promoter type of the pertussis toxin gene.
[2]Fimbrial gene genotype
[3]Pertactin gene allele
[4]Pertussis toxin subunit S1 allele BPZE1 and BPZE1f3 protected equally well against 1617 pF1, 403 pF1, P134 and 403pF3, diminishing the bacterial loads in each case by 4 to 5 logs at 7 days post-infection, compared to the bacterial loads in non-vaccinated mice (FIG. 4). There was no statistically significant difference between BPZE1-vaccinated and BPZE1f3-vaccinated mice. However, when the mice were challenged with 1412pF1, the strain that only produces Fim3 and not Fim2, BPZE1f3 appeared to protect significantly better than BPZE1 (FIG. 4D). Whereas BPZE1 vaccination resulted in a 4 log difference in bacterial load compared to non-vaccinated mice, BPZE1f3 increased this protection to a 5 log difference. No statistically significant decrease in bacterial loads between vaccinated and non-vaccinated mice was observed when the CFU were measured 3 h after challenge infection, indicating that, as expected, all the mice had received the same challenge dose. These results indicate improved potency of BPZE1f3 over BPZE1 against strains that only produce Fim3, whereas there is no improvement in protection against strains that produce Fim2 with or without Fim3, or against strains that do not produce fimbriae.

BPZE1- and BPZE1f3-mediated protection against *Bordetella parapertussis*.

Figure 5:
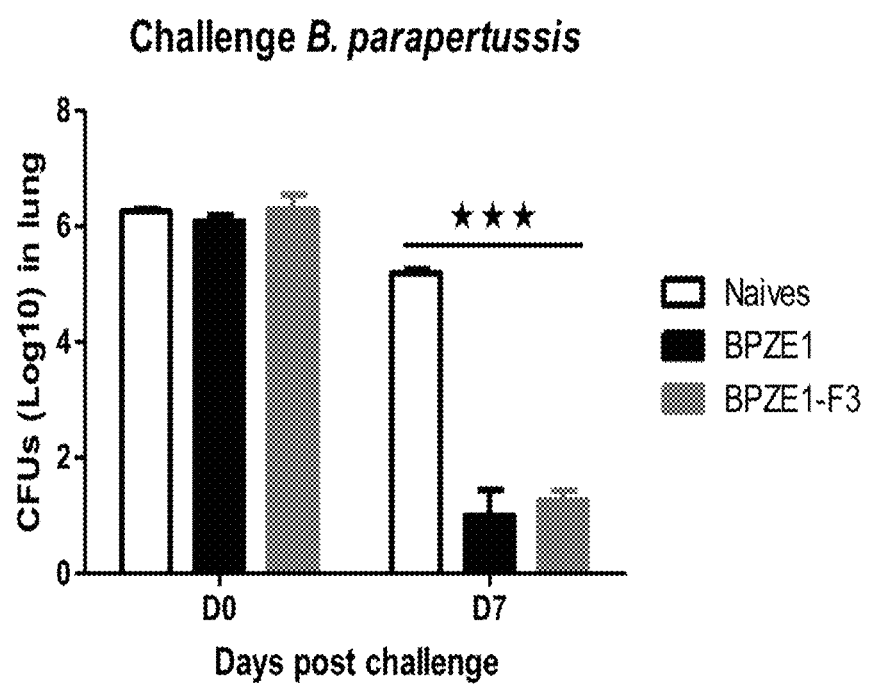
FIG. 5 is a graph comparing BPZE1- and BPZE1f3-induced protection against *B. parapertussis* where mice received nasally either $10^6$ CFU of BPZE1 (black bars) or BPZE1f3 (grey bars), or were left untreated (white bars). Two months after vaccination the mice were challenged with $10^6$ CFU of *B. parapertussis*. Three h (left part of the panel, DO) or 7 days (right part of the panel, D7) after challenge, the bacterial loads in the lungs were measured and are presented as means and standard deviations of CFU. Three (for D0) or five (for D7) mice per group were used. ***, p<0.001.

The potency of BPZE1f3 against *B. parapertussis* was also tested. In this case, $10^6$ CFU of the vaccine strain was used, followed by challenge with $10^6$ CFU of *B. parapertussis* two months after vaccination. It was previously shown that this protocol leads to strong protection, although not to total clearance 7 days after challenge infection (Mielcarek et al., PLoS Pathog 2006; 2:e65). Seven days after *B. parapertussis* infection, both BPZE1- and BPZE1f3-vaccinated mice showed a strong reduction in bacterial load in the lungs (between 4 and 5 logs.) compared to non-vaccinated mice (FIG. 5). No statistical difference was seen between BPZE1- and BPZE1f3-vaccinated mice, indicating that the production of Fim3 does not offer an advantage, nor is it detrimental for protection against *B. parapertussis* infection.

Stability of Fim3 Production by BPZE1f3.

Figure 6:
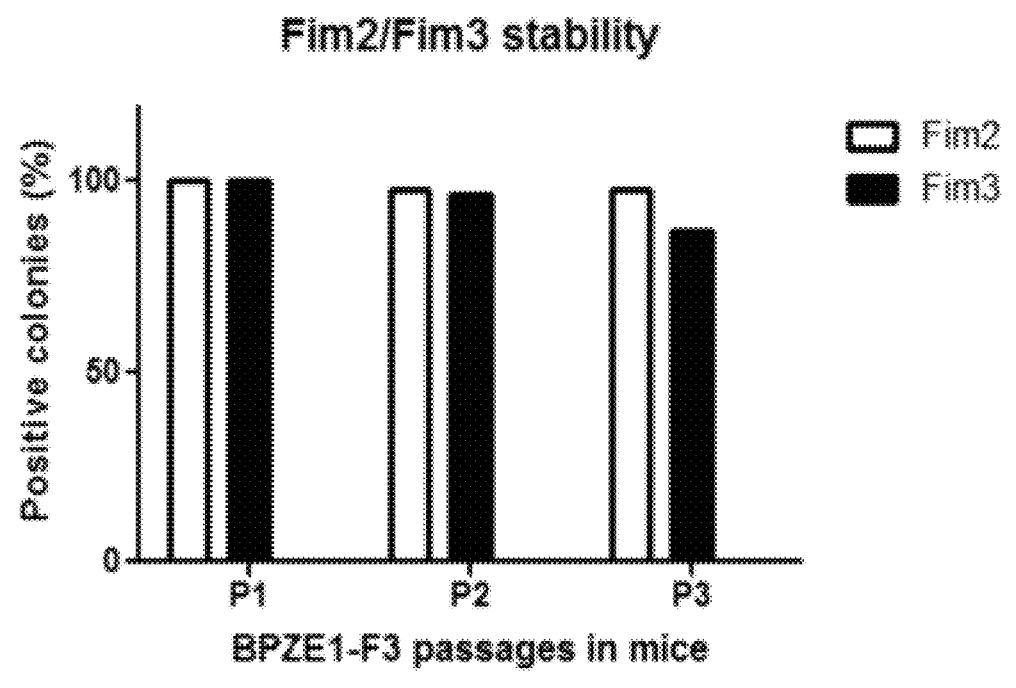

Since the only genetic difference between BPZE1 and BPZE1f3 is the amount of C in the C-string of the fim3 promoter (13 C in BPZE1 and 14 C in BPZE1f3), and since C strings are prone to phase shift variation in *B. pertussis* (Willems et al., EMBO J 1990; 9:2803-9), the stability of both Fim3 and Fim2 production by BPZE1f3 was evaluated after in vivo passaging of the vaccine strain in mice. Mice were infected with $10^6$ CFU of BPZE1f3, and the bacteria present in the lungs 14 days after infection were harvested and plated onto BG agar. After growth, 94 individual colonies were inoculated into a 96-well plate. The remaining colonies were harvested and administered to mice for a second passage, followed 2 weeks later by a third passage. At each passage 94 individual colonies were inoculated into a 96-well plate containing 100 μl of PBS/well. Control wells contained BPZE1, as a negative control, and BPZE1f3 as a positive control. The amount of bacteria present in each well was determined by OD measurement at 630 nm. After drying, the presence of Fim3 and Fim2 was evaluated by whole-cell ELISA. 94 of the 94 clones were found to produce both Fim3 and Fim2 after the first passage. After the second passage 97.9% of the colonies produced Fim2 and 96.8% produced Fim3, and after the third passage the numbers were 87.23% and 97.9% for Fim3 and Fim2, respectively (FIG. 6), indicating a relatively stable fim3 expression, with only 12.77% loss after 3 in vivo passages.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of protecting a mammalian subject from developing pertussis, the method comprising the step of administering to the mammalian subject a vaccine comprising a pharmaceutically acceptable carrier and a live attenuated *Bordetella* strain engineered to stably produce Fim3, wherein the live attenuated *Bordetella* strain retains the ability to colonize the mammalian subject's lungs and induce a protective immune response against *Bordetella* infection.

2. The method of claim 1, wherein the live attenuated *Bordetella* strain stably produces Fim2.

3. The method of claim 1, wherein the live attenuated *Bordetella* strain has been rendered deficient in at least one virulence factor selected from the group consisting of a functional PTX, a functional DNT, and a functional TCT.

4. The method of claim 1, wherein the live attenuated *Bordetella* strain has been rendered deficient in at least two virulence factors selected from the group consisting of a functional PTX, a functional DNT, and a functional TCT.

5. The method of claim 1, wherein the live attenuated *Bordetella* strain has been rendered deficient in a functional PTX, a functional DNT, and a functional TCT.

6. The method of claim 2, wherein the live attenuated *Bordetella* strain has been rendered deficient in at least one virulence factor selected from the group consisting of a functional PTX, a functional DNT, and a functional TCT.

7. The method of claim 2, wherein the live attenuated *Bordetella* strain has been rendered deficient in at least two virulence factors selected from the group consisting of a functional PTX, a functional DNT, and a functional TCT.

8. The method of claim 2, wherein the live attenuated *Bordetella* strain has been rendered deficient in a functional PTX, a functional DNT, and a functional TCT.

9. The method of claim 1, wherein the strain is BPZE1f3 deposited with the Collection Nationale de Cultures de Microorganismes (CNCM) under Registration No. CNCM I-5247.

* * * * *